United States Patent
Grimme

(10) Patent No.: US 11,706,021 B2
(45) Date of Patent: Jul. 18, 2023

(54) METHOD, SERVER AND COMMUNICATION SYSTEM FOR SECURE DELIVERY OF PATIENT'S IMAGE AND CONSENT DATA

(71) Applicant: Siemens Healthcare GmbH, Erlangen (DE)

(72) Inventor: Andreas Grimme, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 583 days.

(21) Appl. No.: 16/415,475

(22) Filed: May 17, 2019

(65) Prior Publication Data

US 2019/0356479 A1 Nov. 21, 2019

(30) Foreign Application Priority Data

May 17, 2018 (EP) ...................... 8172856

(51) Int. Cl.
*H04L 9/08* (2006.01)
*G16H 10/60* (2018.01)
*H04L 9/14* (2006.01)

(52) U.S. Cl.
CPC ........... *H04L 9/0825* (2013.01); *G16H 10/60* (2018.01); *H04L 9/14* (2013.01); *G06Q 2220/12* (2013.01)

(58) Field of Classification Search
CPC ......... H04L 9/0825; H04L 9/14; G16H 10/60; G06Q 2220/12
See application file for complete search history.

(56) References Cited

U.S. PATENT DOCUMENTS

| 2003/0033168 A1* | 2/2003 | Califano | G16H 10/40 705/3 |
| 2009/0049494 A1* | 2/2009 | Freundlich | H04N 21/4122 725/110 |

(Continued)

FOREIGN PATENT DOCUMENTS

| CN | 103763315 A | 4/2014 |
| CN | 104094308 A | 10/2014 |

(Continued)

OTHER PUBLICATIONS

Kamran Ghane, Healthcare Information Exchange System Based on a Hybrid Central/Federated Model, Aug. 1, 2014, IEEE, pp. 1362-1365 (Year: 2014).*

(Continued)

*Primary Examiner* — Neha Patel
*Assistant Examiner* — Nilesh B Khatri
(74) *Attorney, Agent, or Firm* — Banner & Witcoff Ltd.

(57) ABSTRACT

In methods and systems for communicating medical image data that were generated for a patient between computing entities of a hospital network, a cloud-based data store and a patient's mobile device, a QR code serves to code a data package containing a user identification and a public key, which has been generated on the patient's mobile device, to a hospital server, in order to process personal data so that the personal data may be downloaded from the data store directly to the patient's mobile device in an encrypted form, and may be visualized there in clear text by means of applying a private key stored locally on the patient's mobile device. The method and system are web based and need no special requirements on the part of the patient's mobile device.

19 Claims, 3 Drawing Sheets

(56) References Cited

U.S. PATENT DOCUMENTS

| | | | | |
|---|---|---|---|---|
| 2010/0174551 | A1* | 7/2010 | Kiley | G06Q 10/02 |
| | | | | 705/2 |
| 2013/0103847 | A1* | 4/2013 | Brown | H04W 4/21 |
| | | | | 709/229 |
| 2013/0179194 | A1* | 7/2013 | Lorsch | G16Z 99/00 |
| | | | | 705/3 |
| 2014/0095207 | A1* | 4/2014 | Dhir | G16H 10/60 |
| | | | | 705/3 |
| 2014/0156988 | A1* | 6/2014 | Takahashi | H04L 9/321 |
| | | | | 713/155 |
| 2015/0032633 | A1* | 1/2015 | Haider | G06Q 10/06 |
| | | | | 705/51 |
| 2017/0272248 | A1* | 9/2017 | Ozzie | H04L 9/0861 |
| 2017/0277831 | A1* | 9/2017 | Ruff | A61B 6/485 |
| 2017/0303119 | A1* | 10/2017 | Ogura | H04W 12/03 |
| 2018/0233225 | A1* | 8/2018 | Experton | G16H 10/60 |
| 2019/0253243 | A1* | 8/2019 | Zimmerman | H04W 4/70 |

FOREIGN PATENT DOCUMENTS

| | | | | |
|---|---|---|---|---|
| CN | 107644250 | A | 1/2018 | |
| CN | 207068043 | U | 3/2018 | |
| WO | WO-2008026060 | A2 * | 3/2008 | H04L 63/067 |

OTHER PUBLICATIONS

Anonymous: "Chapter 6—Managing Microsoft Certificate Services and SSL"; pp. 1-42; XP055815486; URL:https://docs.microsoft.com/en-us/previous-versions/windows/it-pro/windows-2000-server/bb727098(v=technet.10)?redirectedfrom=MSDN; 2009.
European Examination dated Jun. 25, 2021, Application No. 18 172 856.9.
Chinese Action dated Jul. 15, 2021, Application No. 201910402509.1, with English language translation.
Chinese Action and Search Report dated Dec. 28, 2020, Application No. 201910402509.1, and English translation.
Anonymous: "QR code—Wikipedia"; retrieved from the Internet: URL:https://en.wikipedia.org/w/index.php?title=QR_code&oldid=841275850; retrieved on Oct. 23, 2018; pp. 1-21; XP055518023.
European Search Report dated Nov. 9, 2018, No. 18172856.9-1126.
Yang, Xu et al: "Introduction on Data Science"; Beijing Institute of Technology Press; Jan. 31, 2017, pp. 155-157 (with English translation).

* cited by examiner

METHOD, SERVER AND COMMUNICATION SYSTEM FOR SECURE DELIVERY OF PATIENT'S IMAGE AND CONSENT DATA

BACKGROUND OF THE INVENTION

Field of the Invention

The present invention concerns communicating medical image data and informed patient consent of a patient between a mobile patient device and a hospital network with an imaging device and a hospital server in a secure manner.

Description of the Prior Art

Before a patient undergoes an examination, e.g. with a medical imaging device, he or she needs to give his or her informed consent based upon a clear appreciation and understanding of the facts, implications, and consequences of an examination. The informed consent needs to be documented in a tamper-proof manner.

After the examination, the patient wants to receive the examination results (e.g. DICOM images).

In state of the art systems, the informed patient consent has been documented by archiving a paper "patient consent form," which is filled in and signed by the patient prior to the examination. The content of the consent form is adapted to the particular nature of the examination by having several pre-printed forms on stock or by printing the form on-demand.

A disadvantage of a paper consent form is the infrastructure cost for preparing, stocking, and archiving the paper consent form. Moreover, patients require significant time in order to fill in the form.

After the examination, in state of the art systems, the patient receives physical copies of the examination results. This can be in the form of e.g. paper printouts, film sheets, optical media, or other digital storage media. A disadvantages of delivering the examination data on physical media to the patient is again the infrastructure cost for preparing the physical media. Moreover, staff will need time for preparing and handling the physical media. Another disadvantage is that physical media, when passed to the patient, can be destroyed or damaged. Moreover, the patient or referring physician might not have the required infrastructure for reading the examination data from the physical media.

Thus, in known systems according to state of the art, the informed patient consent as well as the examination results, for example medical images, are exchanged in analog form, for example via printed and signed paper or by a physical data carrier.

In state of the art it is known to provide web-based patient portals where patients and referring physician can log in, in order to retrieve examination data. Disadvantages of these portal-based systems, however, are the unsecure distribution of login credentials and the fact that medical data must be stored on the web server. The web server infrastructure must then comply with the data protection regulations of its respective location.

SUMMARY OF THE INVENTION

An object of the present invention is to improve the above-described known approach regarding communication of patient consent data and examination results. In particular, the disadvantages, mentioned above should be eliminated. Further, data, which include protected health data, should be communicated in a simple but tamper-proof way, and more efficiently without the need of special infrastructure.

According to a first aspect the present invention, a patient's mobile device is used for receiving access to personal medical data in a method that is executed on the patient's mobile device. The method has the following steps.

Via the patient's mobile device, navigating a web client (e.g. via a browser) of the patient's mobile device to a web service.

Instructions are received and reviewed from the (consulted) web service for the web client in order to create a user account, which has an asymmetric key pair and a user identification (UID), which references and is uniquely associated to the asymmetric key pair. The asymmetric key pair is formed by a private key and a public key.

The private key of the asymmetric key pair, and the UID are stored locally on the patient's mobile device.

The public key of the asymmetric key pair is filed—and thus to be transmitted and stored—in a data store under the user identification, acting as key.

A first code is generated based on received instructions from the web service, and is used to encode the UID so the UID is thereby represented in encoded form.

The generated first code is prepared in the patient's mobile device for transmission to a hospital server by using a nearfield data transmission.

Encrypted images, which were encrypted with the public key, are received at the patient's mobile device in response to the hospital server receiving the encrypted user identification.

The received encrypted images are decrypted with the private key locally on the patient's mobile device for providing decrypted personal medical data as a result.

This solution has the advantage that the hospitals and hospital network and infrastructure providers can save significant cost and personnel time that are normally incurred by the infrastructure involved in conventional physical media-based patient consent and image delivery.

In general, the basis of the present invention is, to simplify the information exchange of protected health data (PHI data) by combining simple means, namely a QR-code based method to effortlessly integrate the patient's mobile device into the hospital workflow, together with the method to keep the private encryption key always on the patient's mobile device and thus guaranteeing data protection. If could communication is involved, the cloud itself does not need to fulfill any special requirements or regulations in terms of data protection, which is an enormous advantage as well.

The invention replaces patient consent and examination data delivery based on physical media by a digital, cloud-based solution that makes use of the patient's mobile device. Data security is guaranteed by using asymmetric encryption and keeping the private key on the patient's mobile device at all times.

With the inventive solution, it is possible to offer a purely digital patient consent and data delivery method, which meets all of the requirements relating to security and data protection and further requirements related to the medical domain, and that will appeal to more and more patients as they become familiar with using personal mobile devices. Especially in developing countries, a smart phone is often the only personal computer a patient owns. Therefore, delivering images on a smart phone is superior to delivering images on a CD with built-in Windows-based viewing software when the patients and referring physicians do not own Windows-based PCs.

According to a preferred embodiment of the invention the method is executed as a web client of the web service and is run in a browser on the patient's mobile device. A web service is a software system designed to support interoperable machine-to-machine interaction over a network. It has an interface described in a machine-processable format (e.g. WSDL). Other systems interact with the web service in a manner prescribed by its description using e.g. SOAP-messages, typically conveyed using HTTP with an XML serialization in conjunction with other web-related standards. In an alternative embodiment, the method may be executed as a dedicated mobile application, to be run on a processor of the patient's mobile device.

According to another preferred embodiment of the invention the step of 'navigating' the web client of the patient's mobile device to a web service is executed by accessing a URL link, via which the web service is accessible. For example, a receptionist at the hospital may inform the patient about the link to be used, or the link may be provided to the patient in written form by the receptionist.

Another preferred embodiment for navigating the user to the correct web page is to provide a second code (preferably a QR code) to the patient during his or her registration procedure at the receptionist's desk, and the user of the patient's mobile device scans the provided second (QR) code, which will navigate the user's browser automatically to the correct URL for the web page in order to access the web service.

In another preferred embodiment of the invention, the encrypted images are typically received from a data store to be deployed as a cloud-based data store or cloud server, which is accessible via web technology such as HTTP for transferring machine-readable file formats such as XML and JSON.

In another preferred embodiment of the invention, the personal medical data includes protected health information (PHI) and may include image or other patient examination data or historic anamnestic or other PHI data, which is stored in the data store or cloud server in encrypted form (using the public key of the key pair for encryption). This improves security of the method and system.

In another preferred embodiment of the invention, it is assured that the personal medical data are always transmitted in encrypted form whenever personal medical data leaves the hospital server. This feature also improves the security level.

In another preferred embodiment of the invention, the method further includes receiving a patient consent form on the patient's mobile device that is being uniquely dedicated to the patient's mobile device, based on the extracted user identification. The patient consent form will typically be issued and provided by the hospital server and in particular by a receptionist's computer. This embodiment further includes providing a completed consent form, completed by the patient, and signing the completed consent form with the private key of the generated key pair, provided at the patient's mobile device. The signed completed consent form is then prepared at the patient's mobile device for transmission to the data store, which may preferably be a cloud server.

According to another preferred embodiment, the first code (which is preferably a QR code) encodes the UID and thus indirectly references the patient's public key. This feature has the major technical advantage that only a smaller data volume needs to be transferred from the patient's mobile device to the hospital server, because the UID is much more smaller than a public key of an asymmetric key pair and requires less transmission resources (for storage and bandwidth). A UID is typically 128 bits long whereas the public key of a state of the art asymmetric encryption system is typically 4096 bits long.

According to another preferred embodiment, the nearfield data transmission is a transmission for digital signals. The nearfield data transmission is preferably a wireless data transmission. Different technologies for the nearfield data transmission may be applied with one security requirement, namely requiring a personal contact between the patient at his or her patient mobile device and a user of at the hospital server, in particular a registration server. This assures that misuse and attacks can be prevented. Moreover, an additional security check may be applied by the receptionist requiring the patient to identify herself or himself with another identification object, e.g. an identity card that may be compared with the patient. The nearfield data transmission may be implemented as optical transmission for transmission of the first code. The first code may be a QR code or bar code. Another option is to use other nearfield communication protocols and standards like NFC (nearfield communication), which is a set of protocols, based on radio-frequency identification (RFID) standards including ISO/IEC 14443. NFC communication typically requires a distance of 20 cm or less between the communicating devices. Preferably, passive NFC tags may be used without power supply requirement. In order to provide faster operations, another option is to use a Bluetooth connection, requiring a distance of less than 10 cm. In certain scenarios also Wi-Fi may be used as a technology for wireless local area networking with devices based on the IEEE 802.11 standards.

According to another preferred embodiment, the data store is deployed as cloud server to be accessed via an internet protocol (such as https, https . . . ). In other embodiments, the data store is deployed within a hospital network and is operated by the hospital server. In this case, the data connection between the hospital server and the data store is an internal communication connection. The PHI data stored in the data store will be encrypted so that even in case of an attack, the data will not be compromised.

Another aspect the invention is a method to be executed on the hospital server. The method is intended for providing access to personal medical data and has the steps.

A first code is received by the server, the first code including an encoded UID that identifies a patient's mobile device from which the first code was sent.

The server extracts the UID from the received first code.

The server accesses a data store (which may be a cloud server as mentioned above) with the extracted UID in order to get an associated public key of an asymmetric key pair that was created with involvement of the UID.

The server uses the obtained public in order to for encrypt personal medical data of the patient associated with the UID.

The server sends the encrypted personal medical data to the data store so as to make it accessible by the mobile device of the patient associated with the UID.

In another aspect the invention refers to a method to be executed on a patient's mobile device in communication with a hospital device and thus is to be executed in a distributed manner on both of those devices. The method is intended for communication of personal medical data and has the following steps.

The private key of the asymmetric key pair, and the UID are stored locally on the patient's mobile device.

The public key of the asymmetric key pair is filed—and thus to be transmitted and stored—in a data store under the user identification, acting as key.

A first code is generated based on received instructions from the web service, and is used to encode the UID so the UID is thereby represented in encoded form.

The generated first code is prepared in the patient's mobile device for transmission to a hospital server by using a nearfield data transmission.

The first code is received by the server, the first code, as noted, including an encoded UID that identifies a patient's mobile device from which the first code was sent.

The server extracts the UID from the received first code.

The server accesses a data store (which may be a cloud server as mentioned above) with the extracted UID in order to get an associated public key of an asymmetric key pair that was created with involvement of the UID.

The server uses the obtained public in order to for encrypt personal medical data of the patient associated with the UID.

The server sends the encrypted personal medical data to the data store so as to make it accessible by the mobile device of the patient associated with the UID.

Encrypted images, which were encrypted with the public key, are received at the patient's mobile device in response to the hospital server receiving the encrypted user identification.

The received encrypted images are decrypted with the private key locally on the patient's mobile device for providing decrypted personal medical data as a result.

According to a preferred embodiment the hospital server accesses a Radiology Information System (RIS) in order to calculate an estimated waiting time for a scheduled medical examination for the patient, and this estimating waiting time is transmitted in an estimated-wait-message to the patient's mobile device.

A further aspect the invention IS a hospital server for providing access to personal medical data, wherein the hospital server has a code interface configured to receive a first code, encoding a UID, wherein the UID identifies a patient's mobile device, a processor configured to extract the UID from the received first code, a data store interface configured to access a data store, such as a cloud-based data store, by using the extracted UID in order to get an associated public key of an asymmetric key pair that was created with involvement of the USID. The processor is further configured to use the public key in order to encrypt personal medical data of a patient represented by the UID, and to send encrypted personal medical data to the data store so as to make it accessible by a patient's mobile device of the patient represented by the UID.

Another aspect of the invention is a system for communication of personal medical data between a hospital server and a patient's mobile device, which has a hospital server as described above, and a patient's mobile device with a web client for receiving instructions from a web service as described above, and a data store as described above, in which a public key of the asymmetric key pair has been filed under the UID, acting as key, and in which the personal medical data are stored in encrypted form, having been encrypted with the public key of the asymmetric key pair.

The present invention also encompasses a non-transitory, computer-readable data storage medium encoded with programming instructions that can be loaded into either the patient's mobile device or the hospital server, or can loaded into both devices, so that the programming instructions cause the patient's mobile device and/or the hospital server to implement the methods according to the invention, as described above.

A brief definition of terms, used herein as follows.

The patient's mobile device is a mobile device with computing functionality. It may be a smartphone, a tablet or any other device which is associated to the patient. This device does not require any specific or additional installation of software or hardware. The patient's mobile device is a mobile device owned and operated by the patient or his guardians.

The hospital server is located within a hospital network, where an examination unit is located. The hospital server is a (preferably: mobile) device with internet connectivity owned by the hospital and operated by the receptionist. The hospital server may be the unit itself on which the web service runs. Alternatively, the hospital server may be in data connection to another unit in the hospital network on which the web service runs. The hospital server may preferably be a mobile unit, like a smartphone or a tablet, which may be used by the receptionist of the hospital. Thus, the hospital server is a server owned and operated by the hospital. It needs to have network connectivity to the medical imaging device and/or to the cloud-based data store and internet connectivity.

The data store is an electronic data storage node and may provide physical or virtual storage capacity. The data store may be deployed within the hospital network and operated by the hospital server for different patients. Then, it is assured that each of the different patients will have his or her own partition on the server and that a patient only may get access to his or her personal data. The data store is accessible publicly. In another preferred embodiment the data store is deployed as cloud store and is also accessible via internet from the patient's mobile devices and from the side of the hospital network with the examination units and the hospital server. The PHI data, stored in the data store are encrypted in each of the embodiments mentioned above. The cloud is to be construed as providing elastic cloud services.

The hospital network usually includes a medical imaging device, which is a device that produces examination data (e.g. MRI Scanner, CT device etc.). The produced data are PHI data and need to be transmitted to the patient in a secure and simple manner.

The patient's mobile device interacts with the web service via its browser and executes code, e.g. JavaScript code, which was received from the web service via standardized protocols (e.g. XML, JSON-based protocols, Web Services Conversation Language—WSCL and others).

The first and/or the second code may be provided as a QR code. The first code represents the UID and the second code only serves as a measure to navigate and direct the browser to the web service and to load the respective web service instructions.

The personal medical data are related to the patient and are characterized to be protected. The personal medical data comprise protected health information (PHI data). The personal medical data may be medical examination data (by an imaging examination like CT, MR, etc.), anamnestic data or any kind of other personal data.

The key pair is generated by execution of an asymmetric encryption algorithm and includes a public key and associated private key. The private key will never leave the sphere of the patient's mobile device and will be stored locally on the patient's mobile device. In a preferred embodiment, the private key and/or the decrypted personal data (after being received in encrypted form from the data store) are stored in a secured private storage of the patient mobile device acting as web client. This feature helps to improve security of the system as a whole. The key pair is generated when the patient visits the web service in the hospital for the first time. If he uses the service repeatedly, it is possible to use the generated key pair once more. No new key pair needs to be generated. The user identification (UID) is a unique identifier which uniquely identifies the key pair. It requires less storage than the public key of the key pair.

As noted above, the program code (programming instructions) of the data storage medium in accordance with the invention can be loaded separately into the patient's mobile device and/or the hospital server, and thus the program code is distributively loaded into those devices.

DESCRIPTION OF THE PREFERRED EMBODIMENTS

The present invention relates to systems and methods to replace physical media-based patient consent and image delivery workflows by a purely digital solution while maintaining equal or better data protection.

An important aspect of the invention is the seamless integration of the patient's mobile device via the use of QR-codes and the storage of the private key of the asymmetric encryption on the patient's mobile device only.

The basic workflow is described below with reference to FIG. 1.

Figure 1:
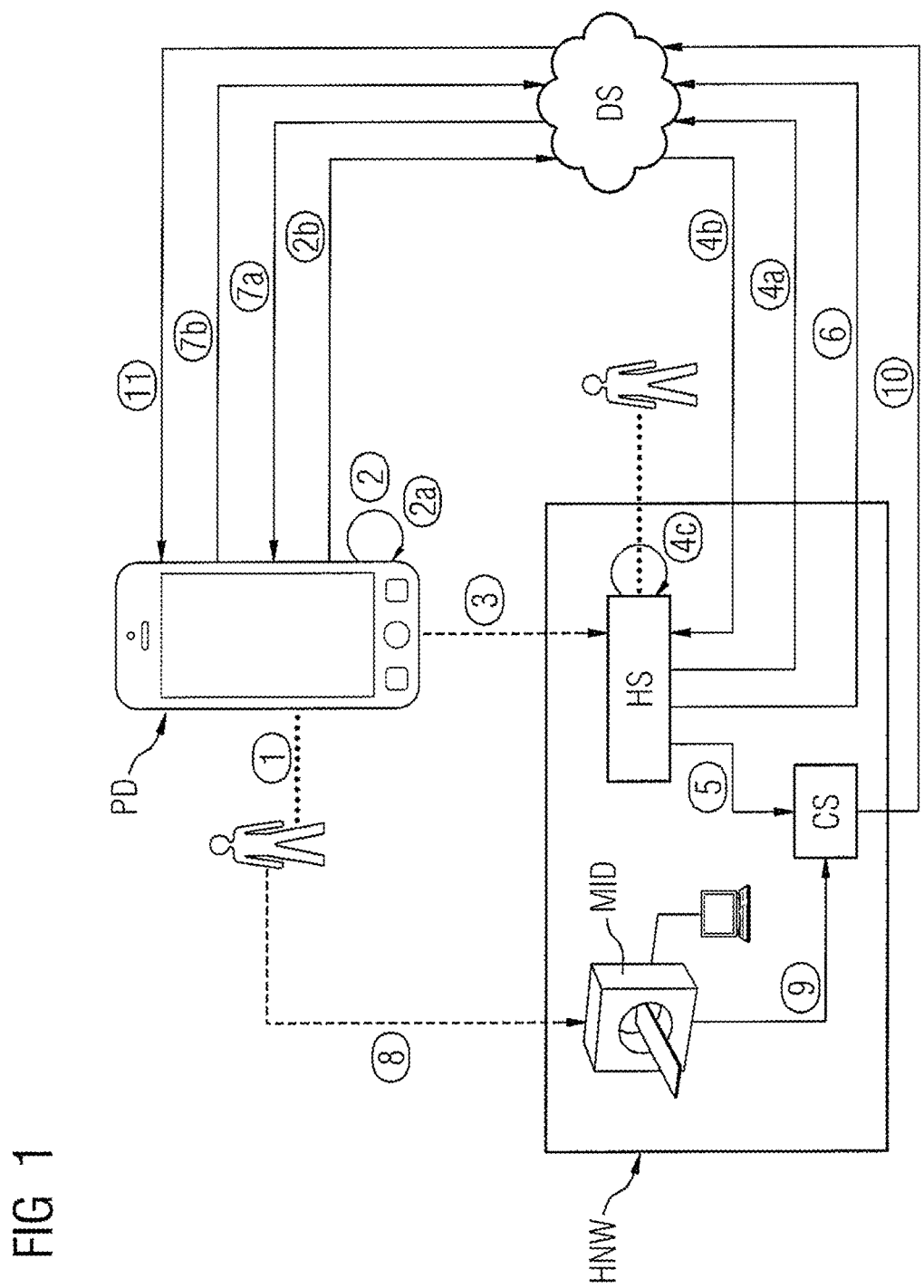
FIG. 1 is a schematic overview figure of the system architecture according to a preferred embodiment of the present invention.

A patient operates his mobile device PD (shown in FIG. 1 above) and a receptionist is operating a hospital server HS, both operating connections are shown in dotted lines in FIG. 1. The dotted lines are, thus, no data connection but should reflect a usage or operation of the respective device PD, HS. The dashed line from patient's mobile device PD to hospital server HS is a data connection different form the other data connection channels shown in normal solid lines. The dashed line should reflect a nearfield communication technology, like a QR code scan transmission via NFC or other protocols, explained in more detail below. The solid lines refer to wireless or wire-bound data transmission via respective protocols.

When the patient visits the hospital to undergo an examination, the patient will bring his or her own mobile device PD with internet connectivity.

The patient will be asked by the receptionist to navigate the browser used by the patient's mobile device to the web portal of the web service, which in FIG. 1 is depicted with reference numeral 1. The user can navigate to the web portal of the service by either entering an URL or by scanning a first code, in particular a QR code, which is displayed in the reception room.

The portal page of the service will instruct the web client of the patient's mobile device PD to create a user account with an asymmetric encryption key pair (Pu=public key, Pr=private key) and a user identification UID. This is depicted in FIG. 1 with reference numeral 2. The user identification UID, and the private key of the asymmetric key pair Pr will be stored in the private data store of the web client. The public key Pu will be filed in a data store DS, which may be implemented as cloud server under key UID. The UID will be displayed as QR code on the portal page.

The receptionist will then scan the QR code, provided with transmission referenced with 3 by the patient, with hospital server HS, which may be provided as mobile device as well. The hospital server HS will file a GET request message to the cloud-based data store DS at 4a. In reply to this GET request, the data store DS will provide the public key Pu filed under UID to the hospital server HS at 4b. In reply to this, the hospital server HS will connect patient's public key Pu and user identification UID with a study ID StudyId generated by e.g. a RIS (radiology information system), which is represented with reference numeral 4c. The tuple (UID, Pu, StudyId) is then sent to a central server CS, referenced in FIG. 1 with 5. The patient data are encrypted with the public key Pu and uploaded to the cloud-based data store DS at 6.

It should be noted that the hospital server HS is preferably provided as mobile device. The hospital server HS, the central sever CS and the Medical Imaging Device MID can be incorporated by a single device. Further, the data store DS is preferably deployed as cloud store. However, it is also possible to locate the data store DS in the hospital network HNW.

While the patient waits for his or her examination, the patient can view the patient information in a provided patient consent form, to be signed by the patient. The patient information, the patient consent form and optionally further information (e.g. a calculated, prognosed waiting time) are provided directly on the patient's mobile device PD, depicted in FIG. 1 with reference numeral 7a. After having received the data package at patient mobile device PD, the patient may read and fill in the form and complete the same in order to prepare a message back. Before sending the message back, it will be encrypted. In particular, the web client on the patient's mobile device PD will sign the patient consent with private key Pr in order to generate the message to be sent to the cloud data store DS. Therefore, the document with the patient consent is transmitted in a tamper-proof way.

At step 8, the patient then undergoes the examination.

In step 9, the Medical Imaging Device MID sends the examination data to the central server CS, using a suitable communication protocol (e.g. DICOM). The central server CS will encrypt the received examination data with the public key Pu and file the encrypted data in step 10 (which means: transmit and store) under user identification UID and (together with) a session identification Sid in the cloud-based data store DS.

After the examination, the patient will download the examination data from the cloud at step 11. After having received the encrypted message, the patient's mobile device PD will decrypt it with the private key Pr, store it locally and view it on the web client or a dedicated mobile application.

Figure 2:
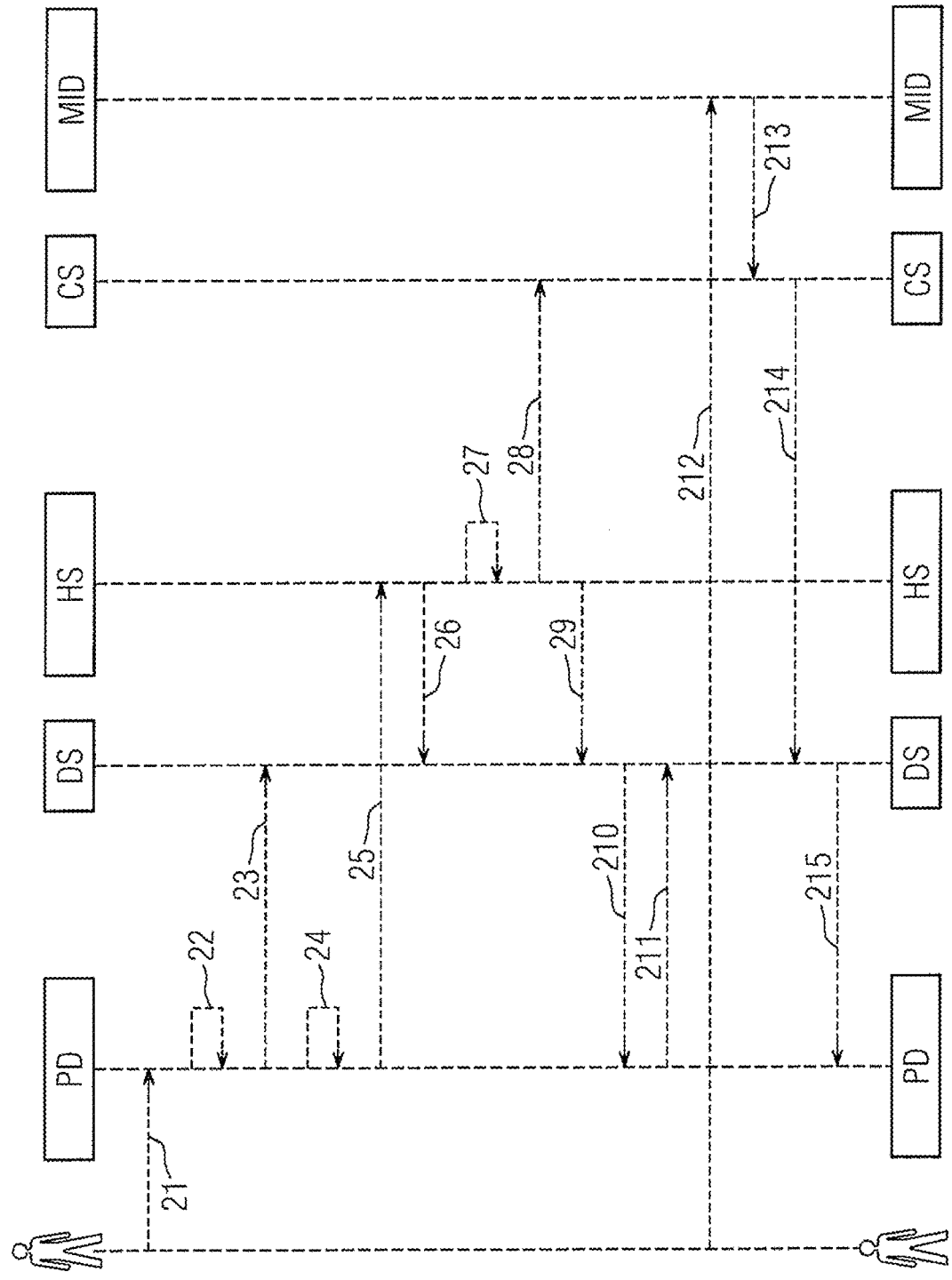
FIG. 2 is an interaction diagram for message transfer between respective devices according to a preferred embodiment of the present invention showing a call flow for communication of personal medical data.

FIG. 2 shows the data exchange in more detail. In step 21 the patient goes to the receptionist and is directed to the web service via an information provided at the receptionist's desk or via a second (preferably QR) code, provided there. In step 22 the key pair is generated with public key Pu, private key Pr and user identification UID. In step 23 the public key Pu is transmitted and filed in the cloud-based data store DS under the user identification UID. In step 24 the private key Pr is stored locally in the web client on the patient's mobile device PD, preferably in a secured storage space.

A first QR code is generated locally at the patient's mobile device PD, comprising the UID. The code may be a QR code, which is transmitted to the hospital server HS, which in reply to the received data message, scans the QR code in step 25 by an optical sensor device. In step 26 the hospital server HS accesses the data store DS in order to get the associated public key Pu, which is stored under the user identification UID. In step 27 the hospital server HS connects the public key Pu with the patient data and generates a tuple with public key Pu and a DICOM StudyIntanceUID, to be sent to the central server CS in step 28. In step 29 the hospital server HS sends an encrypted patient data procedure information (or patient consent form to be completed by the patient) to the data server DS. In step 210 the data store DS sends the encrypted patient data procedure information (or patient consent form to be completed by the patient) to the patient's mobile device PD, where the patient's mobile device may decrypt the data with the private key Pr (not explicitly shown in FIG. 2) and then may read the procedure information in clear text. The patient may complete the patient consent form. The completed patient consent form will then be encrypted again with the private key Pr and will be sent in step 211 to the data store DS.

After the completed patient consent was received in the hospital network system HNW, the patient's examination may be executed in step 212. In step 213 the generated DICOM images will be sent form the medical imaging device MDI to the central server CS. In step 214 the central server CS will send the encrypted DICOM images, being encrypted with the public key Pu, to the data store DS so that the data store DS may forward the encrypted images to the patient's mobile device PD at step 215. Again, at the patient's mobile device PD, the web service will instruct the device PD to decrypt the received data by applying the private key Pr in order to provide the images in clear text on the patient's mobile device PD.

Figure 3:
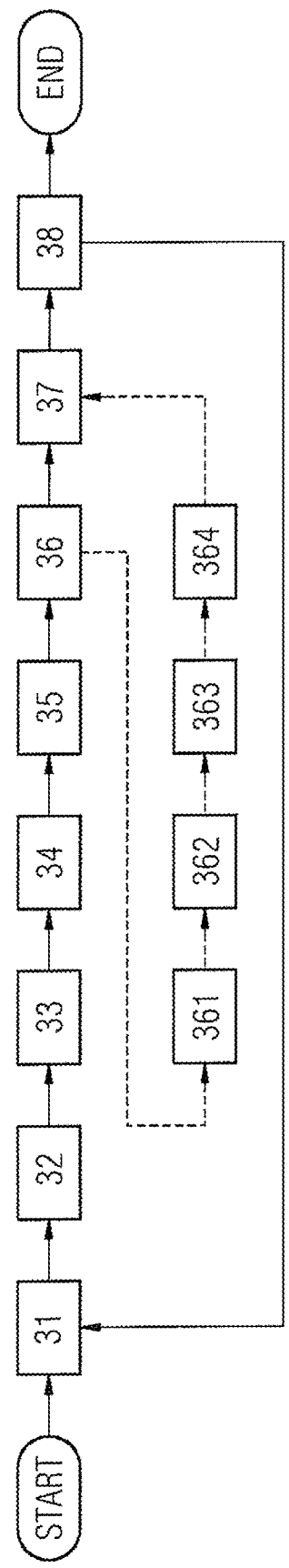
FIG. 3 is a flowchart of a method for receiving personal patient data on the patient's mobile device according to a preferred embodiment of the invention.

FIG. 3 is a flowchart of a method to be executed on the patient's mobile device PD for receiving PHI data, and in particular his examination results. In step 31 the browser of the patient's mobile device PD is navigated to the web service http address. In step 32 instructions are received from the web service for the web client to create a user account, comprising an asymmetric key pair Pu, Pr and a user identification UID. If a user account (Pu, Pr, UID) already exists from a prior session, it may be reused. In step 33 the private key Pr and the user identification UID is stored locally on the patient mobile device PD. In step 34 a data message is generated and prepared for being sent to the data store DS under the user identification UID, acting as key. In step 35 a first code, namely a QR code, is generated, encoding the user identification UID. In step 36, the generated first code is prepared for transmission to a hospital server HS by using a nearfield data transmission, in particular via an optical channel or a digital protocol for nearfield communication, like NFC or Bluetooth, requiring the personal presence of the patient's mobile device (acting as sender) and the (mobile) hospital server HS, operated by the receptionist. In step 37 encrypted images, being encrypted with the public key Pu are received at the patient's mobile device PD, which may be decrypted in step 38 with the private key Pr. After this, the method may end or may be iterated again.

In a preferred embodiment, the method may additionally but optionally comprise the following steps, which are shown in dashed lines in FIG. 3:

receiving, in step 361, a patient consent form on the patient's mobile device PD, being uniquely dedicated to the patient's mobile device, based on extracted user identification UID;

providing, in step 362, a completed consent form;

signing, in step 363, the completed consent form with the private key Pr and preparing, in step 364, the signed completed consent form for transmission to the data store DS.

Figure 4:
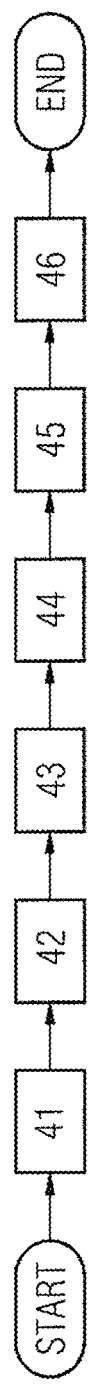
FIG. 4 is a flowchart of a method to be executed on the hospital server according to a preferred embodiment of the invention.

FIG. 4 is a flowchart of a method to be executed on the hospital server HS. After Start, in step 41 a first code, namely the QR code is received from the patient's mobile device PD via the nearfield data communication, requiring personal presence of the patient and the receptionist with their electronic mobile devices PD, HS. In step 42 the user identification UID is extracted from the received first code. In step 43 the data store DS is accessed with the extracted user identification UID for getting the corresponding associated public key Pu of an asymmetric key pair in step 44. In step 45 the personal medical data is encrypted by using the pubic key Pu. In step 46 the encrypted personal medical data is sent to the data store DS for making it accessible by the patient's mobile device PD.

Figure 5:
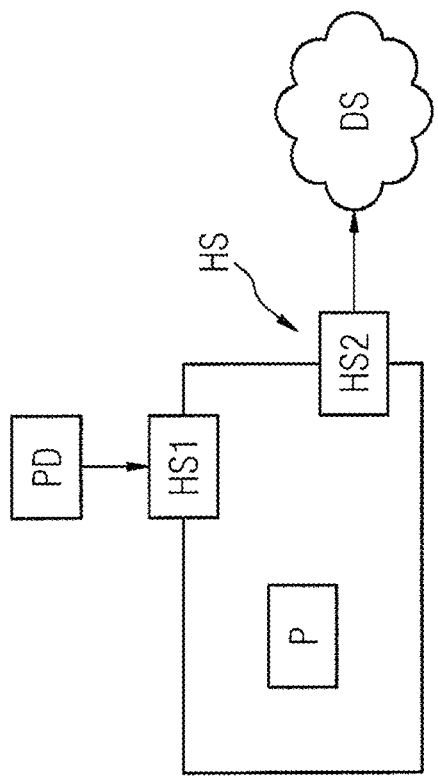
FIG. 5 is a block diagram of a preferred embodiment of a hospital server according to a preferred embodiment of the invention.

FIG. 5 is a block diagram of a hospital server HS in an overview manner. The hospital server may be a mobile electronic device with internet functionality and with interfaces to the hospital network HNW and which may further receive the scanned first code (QR code). In this case, however, additional security requirements have to be met for the mobile device in order to make sure that PHI data, which is at least temporarily stored in clear text on this device cannot be compromised. The hospital server HS comprises a code interface HS1, which is adapted for receiving a first code, encoding a user identification UID, wherein the user identification UID identifies a patient's mobile device PD. The hospital server HS further comprises a processor P for extracting the user identification UID from the received first code and a data store interface HS2 for accessing a data store DS with the extracted user identification UID for getting an associated public key Pu of an asymmetric key pair Pu, Pr, wherein the processor P is further adapted for using the public key Pu for encrypting personal medical data and for sending encrypted personal medical data to the data store DS for making it accessible by the patient's mobile device PD.

While the current invention has been described in relation to its preferred embodiments, it is to be understood that this description is for illustrative purposes only. For example, the hospital server HS may be a mobile device, like a smartphone, a desktop computer or any other technical apparatus with computing functionality, for example being connected to a hospital network system. Other embodiments refer to a hospital server HS which is not mobile and provided as desktop computer of a receptionist. Personal medical data may also refer to any digital data or messages for the patient like previous exams or referencing studies or remarks of a physician. The term may be understood in a broad sense within the medical context. Those skilled in the art will understand that the invention may also be used for other digital processing or services besides patient consent and examination data. Also, the servers need not to be deployed as physical server or server farm. For example, it is also possible that the respective server side functionality described above can be hosted in a virtualized environment as well.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for receiving access to personal medical data, said method being executed on a mobile device and comprising:
navigating a web client of the patient's mobile device to a web service;
receiving instructions from the web service for the web client to create a user account, the user account comprising an asymmetric key pair and a user identification (UID), the asymmetric key pair being formed by a public key and a private key, and the UID identifying the mobile device and referencing the public key of the asymmetric key pair stored in a data store;
storing the private key of the asymmetric key pair and the UID locally on the mobile device;
preparing the public key of the asymmetric key pair to be filed in the data store under the UID, acting as key;
generating a first code that encodes the UID such that the UID is represented in an encoded form and references the public key of the asymmetric key pair, the UID having a bit length that is less than a bit length of the public key;
transmitting only the generated first code in an unencrypted form to a hospital server using a nearfield data transmission;
extracting the UID from the first code to obtain the UID;
accessing the data store with only the UID extracted from the first code to obtain the public key;
encrypting images using only the public key obtained from the data store to generate encrypted images, and storing the encrypted images in the data store;
receiving the encrypted images from the data store; and
decrypting the received encrypted images with the private key to provide decrypted personal medical data on the mobile device.

2. A method according to claim 1, comprising executing the method as a web client with a web browser on the mobile device.

3. A method according to claim 1, comprising navigating the web client of the mobile device to a web service by accessing a Uniform Resource Locator (URL) link, where the web service is accessible.

4. A method according to claim 1, comprising navigating the web client of the mobile device to a web service by scanning a provided second code, which directs the web client to a Uniform Resource Locator (URL) link, where the web service is accessible.

5. A method according to claim 1, wherein the personal medical data comprises protected health information that is stored in the data store in encrypted form.

6. A method according to claim 1, comprising:
receiving a patient consent form on the mobile device, the consent form being uniquely dedicated to the mobile device based on the extracted UID;
providing a completed consent form;
signing the completed consent form with the private key; and
preparing the signed completed consent form for transmission to the data store.

7. A method according to claim 1, wherein the first code encodes the UID so as to indirectly reference the public key of the asymmetric key pair stored in the data store.

8. A method according to claim 1, wherein the nearfield data transmission transmits digital signals conditioned upon a personal presence of a patient identified with the mobile device and a user operating the hospital server.

9. A method according to claim 1, wherein the nearfield data transmission comprises transmitting the generated first code using digital signals via an optical data transmission.

10. A method according to claim 1, comprising using, as the nearfield data transmission, a nearfield data transmission selected from the group consisting of a transmission of a QR code, transmission via a nearfield communication (NFC), and a Bluetooth connection.

11. A method according to claim 1, wherein the data store comprises a cloud server to be accessed via an internet protocol or within a hospital network in which the data store is operated by the hospital server.

12. The method of claim 1, wherein the first code that encodes the UID represents a QR code.

13. The method of claim 1, wherein the first code that encodes the UID represents a barcode.

14. The method of claim 1, wherein the bit length of the UID is 128 bits.

15. A method for providing access to personal medical data, the method being executed on a server, and comprising:
receiving only, a code that represents an unencrypted, encoded encodes a user identification (UID) such that the UID is represented in an encoded form, wherein the UID identifies a mobile device and references a public key stored in a data store, the public key and a private key forming an asymmetric key pair, and the UID identifying the mobile device and having a bit length that is less than a bit length of the public key;
extracting the UID from the received code;
accessing the data store with only the UID extracted from the received code to obtain the associated public key of the asymmetric key pair;
encrypting personal medical data using only the public key obtained from the data store to generate encrypted personal medical data;
and
sending the encrypted personal medical data to the data store so as to make the encrypted personal medical data accessible by the mobile device.

16. A method for communication of personal medical data, comprising:
via a mobile device, navigating a web client of the mobile device to a web service;
receiving instructions at the mobile device from the web service for the web client to create a user account, the user account comprising an asymmetric key pair formed by a public key and a private key, and a user identification (UID), the UID referencing the public key of the asymmetric key pair stored in a data store;
storing the private key of the asymmetric key pair and the UID locally on the mobile device;
at the mobile device, preparing the public key of the asymmetric key pair to be filed in the data store under the UID, acting as key;
at the mobile device, generating a code that encodes the UID such that the UID is represented in an encoded form, wherein the UID identifies the mobile device and references the public key of the asymmetric key pair, the UID having a bit length that is less than a bit length of the public key;

transmitting only the generated code in an unencrypted form from the mobile device to a server using a nearfield data transmission;

at the hospital server, receiving the code;

at the hospital server, extracting the UID from the received code;

at the hospital server, accessing a data store using only the UID extracted from the received code to obtain an associated public key of the asymmetric key pair;

at the hospital server, encrypting personal medical data using only the public key obtained from the data store to generate encrypted personal medical data;

at the hospital server, sending the encrypted personal medical data to the data store so as to make the encrypted personal medical data accessible by the mobile device;

via the mobile device, accessing the data store to receive the encrypted personal medical data that were encrypted with the public key; and at the mobile device, decrypting the received encrypted images with the private key for providing decrypted personal medical data as a result locally on the mobile device.

17. A method according to claim 16, comprising, via the hospital server:

accessing a Radiology Information System to calculate an estimated waiting time for a scheduled medical examination for the patient; and transmitting the estimating waiting time in an estimated-wait-message to the mobile device.

18. A hospital server for providing access to personal medical data, said hospital server comprising:

a code interface configured to receive only a code that represents an unencrypted, encoded user identification (UID) such that the UID is represented in an encoded form, wherein the UID identifies a mobile device and references a public key stored in a data store, the public key and a private key forming, the public key and a private key forming an asymmetric key pair, the UID having a bit length that is less than a bit length of the public key;

a processor configured to extract the UID from the received code; and a data store interface configured to access the data store using only UID extracted from the received code to obtain the associated public key of the asymmetric key pair, wherein the processor is further configured to use only the public key obtained from the data store to encrypt personal medical data to generate encrypted medical data, and to send the encrypted personal medical data to the data store to make the encrypted personal medical data accessible by the mobile device.

19. A system for communication of personal medical data between a hospital server and a mobile device, comprising:

a mobile device with a web client for receiving instructions from a web service;

a data store in which a public key of an asymmetric key pair has been filed under a patient user identification (UID), acting as key, and in which personal medical data of the patient are stored in an encrypted form, the personal medical data being encrypted with the public key of the asymmetric key pair that is formed by the public key and a private key; and a hospital server comprising a code interface configured to receive only a code that represents an unencrypted, encoded user identification (UID) such that the UID is represented in an encoded form, wherein the UID identifies a mobile device and references the public key stored in the data store, the UID having a bit length that is less than a bit length of the public key;

a processor configured to extract the user identification from the received code; and a data store interface configured to access a data store using only the UID extracted from the received code to obtain the associated public key of the asymmetric key pair, wherein the processor is further configured to use only the public key obtained from the data store to encrypt the personal medical data to generate the personal medical data in encrypted form, and to send the personal medical data in encrypted form to the data store to make the encrypted personal medical data in encrypted form accessible by the mobile device.

\* \* \* \* \*